(12) United States Patent
Refardt et al.

(10) Patent No.: US 9,049,866 B2
(45) Date of Patent: Jun. 9, 2015

(54) SYNERGISTIC HERBICIDAL COMBINATION OF CLOMAZONE AND PETHOXAMID

(75) Inventors: Matthias Refardt, Ettingen (CH); Casper Reinhard Christensen, Holstebro (DK)

(73) Assignee: CHEMINOVA A/S, Lemvig (DK)

( * ) Notice: Subject to any disclaimer, the term of this patent is extended or adjusted under 35 U.S.C. 154(b) by 392 days.

(21) Appl. No.: 12/991,499

(22) PCT Filed: May 7, 2009

(86) PCT No.: PCT/DK2009/000105
§ 371 (c)(1),
(2), (4) Date: Nov. 11, 2010

(87) PCT Pub. No.: WO2009/135492
PCT Pub. Date: Nov. 12, 2009

(65) Prior Publication Data
US 2011/0059849 A1    Mar. 10, 2011

(30) Foreign Application Priority Data
May 9, 2008    (DK) .................................. 2008 00667

(51) Int. Cl.
*A01N 43/80*    (2006.01)
*A01N 37/20*    (2006.01)

(52) U.S. Cl.
CPC ..................................... *A01N 43/80* (2013.01)

(58) Field of Classification Search
CPC .... A01N 43/80; A01N 37/20; A01N 2300/00
USPC .......................... 504/138, 140, 271, 342, 111
See application file for complete search history.

(56) References Cited

U.S. PATENT DOCUMENTS

| 4,405,357 A | 9/1983 | Chang |
| 4,895,587 A * | 1/1990 | Kato et al. ..................... 504/289 |
| 5,583,090 A | 12/1996 | Stern et al. |
| 5,597,780 A | 1/1997 | Lee et al. |
| 2003/0069137 A1 | 4/2003 | Almsick et al. |

FOREIGN PATENT DOCUMENTS

| EP | 0 206 251 | 12/1986 |
| WO | WO 2009115433 A2 * | 9/2009 |

OTHER PUBLICATIONS

Colby, S.R., "Calculating Synergistic and Antagonistic Responses of Herbicide Combinations", *Weed Science Society of America*, vol. 15, No. 1, (Jan. 1967), pp. 20-22.

* cited by examiner

*Primary Examiner* — John Pak
*Assistant Examiner* — Andriae M Holt
(74) *Attorney, Agent, or Firm* — Leydig, Voit & Mayer, Ltd.

(57) ABSTRACT

Presented are herbicidal compositions comprising as active ingredients clomazone and pethoxamid. The combinations of these herbicidal active compounds show a synergistic effect in the control of harmful plants.

19 Claims, No Drawings

SYNERGISTIC HERBICIDAL COMBINATION OF CLOMAZONE AND PETHOXAMID

The present invention relates to herbicidal compositions comprising as active ingredients the compound A which is clomazone and the compound B which is pethoxamid. The combinations of these active compounds show a synergistic effect in the control of harmful plants. The invention further relates to a method for the control of harmful plants, such as weeds in crops of useful plants, and to the use of the herbicidal compositions for that purpose.

BACKGROUND

The herbicidal active compound clomazone is known from U.S. Pat. No. 4,405,357 and is generally used to control weeds in various crops. The herbicidal active compound pethoxamid is known from European patent application no. EP 206251-A1 and is generally used to control weeds in various crops such as control of grass weeds and broad-leaved weeds.

Clomazone is known to be a very volatile organic compound to an extend so that clomazone applied in a target area may move to adjacent areas and there cause discoloration, most typically whitening or some degree of bleaching, of a variety of crops, trees, or decorative plants. While this bleaching may be temporary when plants are exposed to sufficiently low concentrations, it is undesirable even when not causing the destruction of the affected plant. Accordingly appropriate use instructions for clomazone is often found on product labels of commercially available clomazone products and in particular on emulsifiable concentrates formulations comprising clomazone in order to prevent exposure to clomazone sensitive plants. Methods of reducing the volatility of clomazone, i.e. to prevent or reduce vapor transfer of clomazone to plants which are not target of application, are proposed in U.S. Pat. Nos. 5,597,780 and 5,583,090 in which encapsulation techniques are applied as to prepare microcapsule suspension formulations of clomazone.

In crop protection products, it is always desirable to increase the specific activity of an active ingredient and the reliability of action. It is an object of the present invention to provide mixtures which comprise a compound A which is clomazone, and the compound B which is pethoxamid which are selective in crops to control undesirable harmful plants. Surprisingly, it has now been found that combinations of these active compounds exhibits a synergistic effect when used for the control of harmful plants. Further it has been found that by combining clomazone with pethoxamid the volatile nature of clomazone is significantly reduced.

DESCRIPTION OF THE INVENTION

In one embodiment, the invention relates to a method for controlling harmful plants comprising exposing said harmful plants to an effective amount of a combination of the compound A which is clomazone, and the compound B which is pethoxamid. In a preferred embodiment the harmful plants are exposed to an effective amount of a synergistic combination of the compound A and the compound B.

In another embodiment, the invention relates to a method for controlling harmful plants in the presence of useful plants comprising exposing said harmful plants and useful plants to an effective amount of a combination of the compound A which is clomazone, and the compound B which is pethoxamid, it being understood that the useful plants remain unharmed after the exposure. In a preferred embodiment the harmful plants are exposed to an effective amount of a synergistic combination of the compound A and the compound B.

In yet another embodiment, the invention relates to a herbicidal composition comprising a herbicidal effective amount of the compound A which is clomazone and the compound B which is pethoxamid. In a preferred embodiment the herbicidal composition comprise a herbicidal effective amount of the compound A and the compound B wherein the active components A and B are present in a synergistically effective amount. The composition is preferably selected among those compositions comprising a form selected from the group consisting of ready-to-use solutions, emulsifiable concentrates, emulsions, suspensions, wettable powders, soluble powders, granules, soluble granules, dispersible granules, microemulsions, microcapsule suspensions and mixtures thereof.

In a further embodiment, the invention relates to a method of reducing the volatility of clomazone, said method comprising combining clomazone as compound A with a compound B which is pethoxamid, preferably in a herbicidal composition as described herein. Preferably the ratio between the compounds A and B is in a ratio as to reduce the volatility of clomazone on a comparative scale to an emulsifiable concentrate composition comprising a similar amount of clomazone and without the compound B being present. Preferable compounds A and B are present in a herbicidal effective amount but the compound B need not necessarily be present so as to produce a synergistic effect with the compound A. However, in a very preferred embodiment, the method of reducing the volatility of clomazone comprise combining clomazone as compound A with a compound B which is pethoxamid, in a ratio as to reduce the volatility of the clomazone while maintaining a synergistic herbicidal effect and without substantially sacrificing the overall herbicidal activity. Such ratios are preferably as herein described. Thus, the present invention relates to a herbicidal composition having reduced clomazone vapour transfer comprising a compound A which is clomazone and a compound B which is pethoxamid and preferably the composition comprise a herbicidal effective amount of the compound A and the compound B wherein the active components A and B are present in a synergistically effective amount. Such ratios and amounts are preferably as herein described.

The compositions according to the invention can be employed for the selective control of grasses and annual and perennial monocotyledonous and dicotyledonous harmful plants the presence of useful plants such as maize, soya, peas, beans, sunflowers, oilseed rape, sugar cane, cassava, pumpkins, potatoes, vegetables and tobacco. Within the scope of this invention is also the control of such harmful plants found among transgenic useful plants or among useful plants selected by classical means which are resistant to the active compounds A and B. Likewise, the compositions can be employed for controlling undesirable harmful plants in plantation crops. Among harmful plants, e.g. weeds or volunteer crop plants, that may be controlled are *Ambrosia artemisiifolia, Amaranthus retroflexus, Apera spica-venti, Capsella bursa-pastoris, Chenopodium album, Convolvulus arvensis, Digitaria ischaemum, Digitaria sanguinalis, Echinochloa crus-galli, Galium aparine, Lamium purpureum, Matricaria* spp., *Mercurialis annua, Myosotis arvensis, Poa* spp., *Polygonum convolvulus, Polygonum persicaria, Portulaca oleracea, Senecio vulgaris, Setaria geniculata, Solanum nigrum, Stellaria media, Veronica persica* and *Viola arvensis.*

Compositions containing the active compounds A and B may be employed in any conventional form, for example, in the form of a twin pack, or ready-to-use solutions, emulsifiable concentrates, emulsions, suspensions, wettable powders, soluble powders, granules, soluble granules, dispersible granules, microemulsions, microcapsule suspensions e.g. capsules comprising both active ingredients or present within separate capsules; and mixtures thereof such as a ZC, ZE or ZW formulation. Such compositions can be formulated using adjuvants and formulation techniques that are known in the art for individually formulating the herbicides. For example, the herbicides may be mixed together, optionally with other formulating ingredients.

The compositions may contain a diluent, which may be added during the formulation process, after the formulation process (e.g. by the user—a farmer or custom applicator), or both. The term diluent includes all liquid and solid agriculturally acceptable material-including carriers which may be added to the herbicides to bring them in a suitable application or commercial form and include solvents, emulsifiers, and dispersants. Examples of suitable solid diluents or carriers are aluminum silicate, talc, calcined magnesia, kieselguhr, tricalcium phosphate, powdered cork, absorbent carbon black, chalk, silica, and clays such as kaolin and bentonite. Examples of suitable liquid diluents include water, organic solvents (e.g. acetophenone, cyclohexanone, isophorone, toluene, xylene, petroleum distillates), amines (e.g. ethanolamine, dimethylformamide), and mineral, animal, and vegetable oils (used alone or in combination). The compositions may also contain surfactants, protective colloids, thickeners, penetrating agents, stabilizers, sequestering agents, anti-caking agents, coloring agents, corrosion inhibitors, and dispersants such as lignosulfite waste liquors and methylcellulose. The term surfactant, as used herein, means an agriculturally acceptable material which imparts emulsifiability, stability, spreading, wetting, dispersibility or other surface-modifying properties. Examples of suitable surfactants include lignin sulfonates, fatty acid sulfonates (e.g. lauryl sulfonate), the condensation product of formaldehyde with naphthalene sulfonate, alkylarylsulfonates, ethoxylated alkylphenols, and ethoxylated fatty alcohols. Other known surfactants that have been used with herbicides are also acceptable.

When mixed with additional components, the composition typically contain about 0.01 to about 95% by weight of active compounds, about 0 to about 20% agriculturally acceptable surfactants, and about 5 to 99.99% solid or liquid diluent(s). The compositions may additionally contain other additives known in the art, such as pigments, thickeners and the like.

The compositions may be applied in various combinations of the two active compounds. For example, they may be applied as a single "ready-mix" form, or in a combined spray mixture composed from separate formulations of the active compounds, e.g. a "tank-mix" form. Thus, to be used in combination, it is not necessary that the two herbicides, be applied in a physically combined form, or even at the same time, i.e. the components may be applied in a separately and/or sequentially application, provided that the application of the second active compound occurs within a reasonable period of time from the application of the first active compound. The combination effect results so long as the two herbicides are present at the same time, regardless of when they were applied. Thus, for instance, a physical combination of the two herbicides could be applied, or one could be applied earlier than the other so long as the earlier-applied herbicide is still present on the harmful plant to be controlled or in the soil surrounding the harmful plant to be controlled when the second is applied, and so long as the weight ratio of available herbicides falls within that provided herein. The order of applying the individual components A and B is not essential. Likewise, any form of combination of the active components may be applied for either pre- or post-emergence control of harmful plants, e.g. weeds in crops of useful plants.

Rates of application of the composition will vary according to prevailing conditions such as targeted weeds, degree of infestation, weather conditions, soil conditions, crop species, mode of application, and application time. Compositions containing the active compounds may be applied in the manner, which they are formulated, as discussed above. For example, they may be applied as sprays, such as water-dispersible concentrates, wettable powders, or water-dispersible granules.

The weight ratio of component A to component B is preferably selected to provide a synergistic herbicidal action. Such amounts are also called synergistically effective amounts and can easily be determined by the skilled person using well known principles. In general, the weight ratio of A:B ranges from about 1:1 to about 1:30, preferably 1:5 to 1:25 and more preferably 1:8 to 1:20 and most preferably 1:10 to 1:15. The weight ratio of A:B will depend on various factors such as the mode of application, the harmful plants to be combated, the useful plant to be protected, the application time, etc.

An effective amount of A and B is any amount that has the ability to combat the harmful plants. In general, satisfactory results will be obtained when employing from about 1 to about 300 g/ha, preferably 10 to about 200 g/ha of compound A, and more preferably from about 50 to about 150 g/ha; and from about 100 to about 3000 g/ha, preferably about 500 to about 2500 g/ha of the compound B, and more preferably from about 800 to about 1500 g/ha. However, higher and in particular lower doses may also provide adequate control.

Additional herbicides may be also be used, preferably so provided that the additional herbicide does not interfere with the synergistic relationship between the compound A herbicide and the compound B. An additional herbicide may be utilized if broadening of the spectrum of control or preventing the build-up of resistance is desired.

Examples of additional herbicides are acetyl-CoA carboxylase inhibitors (ACC), for example cyclohexenone oxime ethers, such as alloxydim, clethodim, cloproxydim, cycloxydim, sethoxydim, tralkoxydim, butroxydim, clefoxydim or tepraloxydim; phenoxyphenoxypropionic esters, such as clodinafop-propargyl, cyhalofopbutyl, diclofop-methyl, fenoxaprop-ethyl, fenoxaprop-P-ethyl, fenthiapropethyl, fluazifop-butyl, fluazifop-P-butyl, haloxyfop-ethoxyethyl, haloxyfopmethyl, haloxyfop-P-methyl, isoxapyrifop, propaquizafop, quizalofop-ethyl, quizalofop-P-ethyl or quizalofop-tefuryl; or arylaminopropionic acids, such as flamprop-methyl or flamprop-isopropyl; p-hydroxyphenylpyruvatdioxygenase (HPPD)-inhibitors, for example pyrazolynate, pyrazoxyfen, benzofenap, sulcotrione, isoxaflutole, mesotrione, isoxachlortole, ketospiradox, tembotrione; acetolactate synthase inhibitors (ALS), for example imidazolinones, such as imazapyr, imazaquin, imazamethabenz-methyl (imazame), imazamox, imazapic or imazethapyr; pyrimidyl ethers, such as pyrithiobac-acid, pyrithiobac-sodium, bispyribac-sodium or pyribenzoxym; sulfonamides, such as cloransulam, diclosulam, florasulam, flumetsulam, metosulam or penoxsulam; or sulfonylureas, such as amidosulfuron, azimsulfuron, bensulfuron-methyl, chlorimuronethyl, chlorsulfuron, cinosulfuron, cyclosulfamuron, ethametsulfuron-methyl, ethoxysulfuron, flazasulfuron, foramsulfuron, halosulfuron-methyl, imazosulfuron, iodosulfuron, metsulfuron-methyl, nicosulfuron, primisulfuron-methyl, prosulfuron, pyrazosulfuronethyl, rimsulfuron, sulfometuron-methyl or -3-oxetanyl, sulfosulfuron, thifensulfuron-methyl, triasulfuron, tribenuron-methyl, triflusulfuron-methyl or tritosulfuron; amides, for example allidochlor, benzoylprop-ethyl, bromobutide, chlorthiamid, diphenamid, etobenzanid (benzchlomet), fluthiamide, fosamin or monalide; auxin herbicides, for example pyridinecarboxylic acids, such as clopyralid or picloram; 2,4-D or benazolin; auxin transport inhibitors, for example naptalame or diflufenzopyr; carotenoid biosynthesis inhibitors, for example amitrol, diflufenican, fluorochloridone, fluridone, flurtamone, norflurazon or picolinafen; enolpyruvylshikimate-3-phosphate synthase inhibitors (EPSPS), for example glyphosate or sulfosate; glutamine synthetase inhibitors, for example bilanafos (bialaphos) or glufosinate-ammonium; lipid biosynthesis inhibitors, for example anilides, such as anilofos or mefenacet; chloroacetanilides, such as dimethenamid, S-dimethenamid, acetochlor, alachlor, butachlor, butenachlor, diethatyl-ethyl, dimethachlor, metazachlor, metolachlor, Smetolachlor, pretilachior, propachlor, prynachlor, terbuchlor, thenylchlor or xylachlor; thioureas, such as butylate, cycloate, di-allate, dimepiperate, EPTC, esprocarb, molinate, pebulate, prosulfocarb, thiobencarb (benthiocarb), tri-allate or vernolate; or benfuresate or perfluidone; mitosis inhibitors, for example carbamates, such as asulam, carbetamid, chlorpropham, orbencarb, propyzamid, propham or tiocarbazil; dinitroanilines, such as benefin, butralin, dinitramin, ethalfluralin, fluchloralin, oryzalin, pendimethalin, prodiamine or trifluralin; pyridines, such as dithiopyr or thiazopyr; or butamifos, chlorthal-dimethyl (DCPA) or maleic hydrazide; protoporphyrinogen IX oxidase inhibitors, for example diphenyl ethers, such as acifluorfen, acifluorfen-sodium, aclonifen, bifenox, chlornitrofen (CNP), ethoxyfen, fluorodifen, fluoroglycofen-ethyl, fomesafen, furyloxyfen, lactofen, nitrofen, nitrofluorfen or oxyfluorfen; oxadiazoles, such as oxadiargyl or oxadiazon; cyclic imides, such as azafenidin, butafenacil, carfentrazone-ethyl, cinidon-ethyl, flumiclorac-pentyl, flumioxazin, flumipropyn, flupropacil, fluthiacet-methyl, sulfentrazone or thidiazimin; or pyrazoles, such as ET-751, JV 485 or nipyraclofen; photosynthesis inhibitors, for example propanil, pyridate or pyridafol; benzothiadiazinones, such as bentazone; dinitrophenols, for example bromofenoxim, dinoseb, dinoseb-acetate, dinoterb or DNOC; dipyridylenes, such as cyperquat-chloride, difenzoquat-methylsulfate, diquat or paraquat-dichloride; ureas, such as chlorbromuron, chlorotoluron, difenoxuron, dimefuron, diuron, ethidimuron, fenuron, fluometuron, isoproturon, isouron, linuron, methabenzthiazuron, methazole, metobenzuron, metoxuron, monolinuron, neburon, siduron or tebuthiuron; phenols, such as bromoxynil or ioxynil; chloridazon; triazines, such as ametryn, atrazine, cyanazine, desmetryn, dimethamethryn, hexazinone, prometon, prometryn, propazine, simazine, simetryn, terbumeton, terbutryn, terbutylazine or trietazine; triazinones, such as metamitron or metribuzin; uracils, such as bromacil, lenacil or terbacil; or biscarbamates, such as desmedipham or phenmedipham; growth substances, for example aryloxyalkanoic acids, such as 2,4-DB, clomeprop, dichlorprop, dichlorprop-P (2,4-DP-P), fluoroxypyr, MCPA, MCPB, mecoprop, mecoprop-P or triclopyr; benzoic acids, such as chloramben or dicamba; or quinolinecarboxylic acids, such as quinclorac or quinmerac; cell wall synthesis inhibitors, for example isoxaben or dichiobenil; various other herbicides, for example dichloropropionic acids, such as dalapon; dihydrobenzofurans, such as ethofumesate; henylacetic acids, such as chlorfenac (fenac); or aziprotryn, barban, bensulide, benzthiazuron, benzofluor, buminafos, buthidazole, buturon, cafenstrole, chlorbufam, chlorfenprop-methyl, chloroxuron, cinmethylin, cumyluron, cycluron, cyprazine, cyprazole, dibenzyluron, dipropetryn, dymron, eglinazin-ethyl, endothall, ethiozin, flucabazone, fluorbentranil, flupoxam, isocarbamid, isopropalin, karbutilate, mefluidide, monuron, napropamide, napropanilide, nitralin, oxaciclomefone, phenisopham, piperophos, procyazine, profluralin, pyributicarb, secbumeton, sulfallate (CDEC), terbucarb, triaziflam, triazofenamid or trimeturon; or their environmentally compatible salts, "acids", esters and amides.

The compounds A and B and optionally one or more additional herbicides may also be applied in combination with at least one safener compound. A safener compound is a compound, which is effective for antagonism the herbicides A, B or both or the optional additional herbicide(s), and which is applied in a suitable amount i.e., an amount which counteracts to some degree a phytotoxic response of a useful plant to the herbicide(s). The safener may suitably be incorporated in the composition discussed above. Safeners suitable for use include cloquintocet, cloquintocet-mexyl, benoxacor, dichlormid, fenchlorazole-ethyl, fenclorim, flurazole, fluxofenim, furilazole, isoxadifen, isoxadifen-ethyl, mefenpyr, mefenpyrdiethyl and oxabetrinil or their environmentally compatible salts, "acids", esters and amides.

A synergistic effect exists whenever the action of a combination of active components is greater than the sum of the action of each of the components alone. Therefore, a synergistic combination is a combination of active components having an action that is greater than the sum of the action of each active component alone, and a synergistically effective amount is an effective amount of a synergistic combination. Well-known methods for determining whether synergy exists include the Colby method, the Tammes method and the Wadley method, all of which are described below. Any one of these methods may be used to determine if synergy exists between the compounds A and B.

In the Colby method, also referred to as the Limpels method, the action to be expected E for a given active ingredient combination obeys the so-called Colby formula. According to Colby, the expected action of active ingredients A+B using p+q ppm of active ingredient is:

$$E = X + Y - \frac{X \cdot Y}{100}$$

where ppm=milligrams of active ingredient (=a.i.) per liter of spray mixture X=% action by component A using p ppm of active ingredient Y=% action by component B using q ppm of active ingredient. If the ratio R defined as the action actually observed (O) divided by the expected action (E) is >1 then the action of the combination is superadditive, i.e. there is a synergistic effect. For a more detailed description of the Colby formula, see Colby, S. R. "Calculating synergistic and antagonistic responses of herbicide combination," Weeds, Vol. 15, pages 20-22; 1967; see also Limpel et al., Proc. NEWCC 16: 48-53 (1962).

The Tammes method uses a graphic representation to determine whether a synergistic effect exists. See "Isoboles, a graphic representation of synergism in pesticides," Netherlands Journal of Plant Pathology, 70 (1964) p. 73-80.

The Wadley method is based on comparison of an observed EC50 value (i.e concentration providing 50% control) obtained from experimental data using the dose response curves and an expected EC50 calculated theoretically from the formula:

$$EC50(A+B)_{exp} = \frac{a+b}{\frac{a}{EC50(A)_{obs}} + \frac{b}{EC50(B)_{obs}}}$$

wherein a and b are the weight ratios of compound A and B in the mixture and EC50obs is the experimentally determined EC50 value obtained using the dose response curves for the individual compounds. The ratio EC50(A+B)expected/EC50 (A+B) observed expresses the factor of interaction (F) (synergy factor). In case of synergism, F is >1. For a more detailed description of the Wadley method, see Levi et al., EPPO-Bulletin 16, 1986, 651-657.

The invention is illustrated by the following examples:

The herbicidal compounds A and B were applied in the formulation in which they are present as commercially available product. Damage by the herbicidal compositions was evaluated with reference to a scale of 0% to 100% in comparison with untreated control plots. 0 means no damage and 100 means complete destruction of the harmful plants.

Example 1

In a field of sunflowers, clomazone (rate of 90 g/ha) and pethoxamid (rate of 1200 g/ha) were applied individually and in combination (90+1200 g/ha) to different plots by spraying. 55 days after application the rate of control of various weeds was recorded. Results are provided in table 1. The expected control is calculated according to the Colby method.

TABLE 1

| Weed | Active substance (AI) | Control observed (O) % | Expected control (E) % |
|---|---|---|---|
| Echinochloa crus-galli | Clomazone | 50 | |
| | Pethoxamid | 47 | |
| | Clomazone + Pethoxamid | 94 | 74 (1.28) |
| Solanum nigrum | Clomazone | 37 | |
| | Pethoxamid | 47 | |
| | Clomazone + Pethoxamid | 87 | 67 (1.31) |

( ) indicates the synergism ratio R.

Example 2

In a field of sunflowers, clomazone (rate of 90 g/ha) and pethoxamid (rate of 1200 g/ha) were applied individually and in combination (90+1200 g/ha) to different plots by spraying. 50 days after application the rate of control of various weeds was recorded. Results are provided in table 2. The expected control is calculated according to the Colby method.

TABLE 2

| Weed | Active substance (AI) | Control observed (O) % | Expected control (E) % |
|---|---|---|---|
| Mercurialis annua | Clomazone | 13 | |
| | Pethoxamid | 27 | |
| | Clomazone + Pethoxamid | 76 | 37 (2.08) |
| Ambrosia artemisiifolia | Clomazone | 10 | |
| | Pethoxamid | 10 | |
| | Clomazone + Pethoxamid | 100 | 19 (5.26) |

Example 3

In an oilseed rape field, Clomazone, and pethoxamid were applied individually and in combination to different plots by spraying. 206 days after application the rate of control of *Viola arvensis* was recorded. Results are provided in table 3. The expected control is calculated according to the Colby method.

TABLE 3

| Active substance (AI) | g. AI/ hectare | Control observed (O) % | Expected control (E) % |
|---|---|---|---|
| Clomazone | 72 | 0 | |
| Pethoxamid | 1200 | 50 | |
| Clomazone + Pethoxamid | 72 + 1200 | 63 | 50 (1.26) |

( ) indicates the synergism ratio R.

Example 4

In an oilseed rape field, Clomazone, and pethoxamid were applied individually and in combination to different plots by spraying. 64 days after application the rate of control of *Galium aparine* was recorded. Results are provided in table 4. The expected control is calculated according to the Colby method.

TABLE 4

| Active substance (AI) | g. AI/ hectare | Control observed (O) % | Expected control (E) % |
|---|---|---|---|
| Clomazone | 72 | 40 | |
| Pethoxamid | 1200 | 0 | |
| Clomazone + Pethoxamid | 72 + 1200 | 81 | 40 (2.03) |

( ) indicates the synergism ratio R.

Example 5

The volatility of clomazone in clomazone/pethoxamid mixtures as well as straight clomazone in emulsifiable concentrate (EC) and microcapsule suspension (CS) formulations was tested. The following formulations were prepared, wherein the microcapsule suspensions are mixtures of microcapsules comprising the individual active ingredients:

TABLE 5

| Formulation type | a.i. content: |
|---|---|
| 1 - (CS) | 400 g/l pethoxamid + 35 g/l clomazone |
| 2 - (EC) | 400 g/l pethoxamid + 24 g/l clomazone |
| 3 - (CS) | 360 g/l clomazone |
| 4 - (EC) | 500 g/l clomazone |

Test plants (newly germinated wheat seeds; Vinjet) were planted in 81 cm$^3$ pots. 30 ml formulation (diluted as to comprise 0.5 g/l of clomazone) in small glass bowls was placed at the bottom of each of the four desiccator jars. Plants were placed in petri dishes with moistened filter paper. In every desiccator, four pots of wheat were placed on the top of the plates and each trial setup was covered with the desiccator lid (open at the top). After 72 hours, the plants were removed from the desiccators. The development of foliar injury due to clomazone vapor was evaluated and scored visually after 7 and 11 days (average). Clomazone caused easily notable foliar injuries such as bleaching and tip-burning. Results are provided in the below table

TABLE 6

| Formulation | % Phytotoxicity | |
| --- | --- | --- |
| | Day 7 | Day 11 |
| Control (no a.i.) | 0 | 0 |
| 1 - (CS) - pethoxamid + clomazone | 33 | 41 |
| 2 - (EC) - pethoxamid + clomazone | 25 | 23 |
| 3 - (CS) - clomazone | 75 | 85 |
| 4 - (EC) - clomazone | 78 | 65 |

Plants exposed to formulations containing only clomazone showed a higher level of foliar injury than plants exposed to mixtures of pethoxamid and clomazone.

The invention claimed is:

1. A method for controlling harmful plants comprising exposing the harmful plants to a synergistically effective amount of a combination of compound A and compound B, wherein compound A is clomazone, compound B is pethoxamid, and the method comprises applying from 10 to 200 g/ha of compound A and from 100 to 3000 g/ha of compound B in a weight ratio of compounds A:B ranging from 1:5 to 1:25 to the harmful plants, wherein clomazone and pethoxamid are the only active herbicidal compounds in the combination.

2. A method according to claim 1, wherein the harmful plants are present together with useful plants.

3. The method according to claim 2, wherein the useful plants are selected from the group consisting of maize, soya, pea, bean, sunflower, oilseed rape, sugar cane, cassaya, pumpkin, potato, vegetables and tobacco.

4. The method according to claim 1, wherein the harmful plants are selected from the group consisting of grasses, annual and perennial monocotyledonous and dicotyledonous plants.

5. The method according to claim 1, comprising applying from 500 to 2500 g/ha of compound B.

6. The method according to claim 1, comprising applying from 50 to 150 g/ha of compound A and from 800 to 1500 g/ha of compound B.

7. The method according to claim 1, wherein the weight ratio of compounds A:B ranges from 1:8 to 1:20.

8. The method according to claim 1, wherein the weight ratio of compounds A:B ranges from 1:10 to 1:15.

9. The method according to claim 1, comprising applying 90 g/ha of compound A and 1200 g/ha of compound B.

10. The method according to claim 1, comprising applying 72 g/ha of compound A and 1200 g/ha of compound B.

11. A synergistic herbicidal composition comprising compound A and compound B, wherein compound A is clomazone, compound B is pethoxamid, and the weight ratio of compounds A:B ranges from 1:5 to 1:25, wherein clomazone and pethoxamid are the only active herbicidal compounds in the composition.

12. A composition according to claim 11, wherein compound A and compound B are present in a form selected from the group consisting of ready-to-use solutions, emulsifiable concentrates, emulsions, suspensions, wettable powders, soluble powders, granules, soluble granules, dispersible granules, microemulsions, microcapsule suspensions and mixtures thereof.

13. The composition according to claim 11, wherein the weight ratio of compounds A:B ranges from 1:8 to 1:20.

14. The composition according to claim 11, wherein the weight ratio of compounds A:B ranges from 1:10 to 1:15.

15. A method for reducing the volatility of clomazone, the method comprising combining a synergistically effective amount of compound A and an amount of compound B effective to reduce the volatility of compound A, wherein compound A is clomazone, compound B is pethoxamid, and the weight ratio of compounds A:B ranges from 1:5 to 1:25, wherein clomazone and pethoxamid are the only active herbicidal compounds.

16. The method according to claim 15, wherein the weight ratio of compounds A:B ranges from 1:8 to 1:20.

17. The method according to claim 15, wherein the weight ratio of compounds A:B ranges from 1:10 to 1:15.

18. The method according to claim 15, comprising applying 35 g/l of compound A and 400 g/l of compound B.

19. The method according to claim 15, comprising applying 24 g/l of compound A and 400 g/l of compound B.

* * * * *